(12) United States Patent
Ness et al.

(10) Patent No.: US 9,872,980 B2
(45) Date of Patent: Jan. 23, 2018

(54) SYSTEMS AND METHODS FOR MONITORING CHARGE DENSITY OF ELECTRICAL STIMULATION

(71) Applicant: PACESETTER, INC., Sylmar, CA (US)

(72) Inventors: Lanitia Ness, Los Angeles, CA (US); Martin Cholette, Van Alstyne, TX (US)

(73) Assignee: PACESETTER, INC., Sylmar, CA (US)

( * ) Notice: Subject to any disclaimer, the term of this patent is extended or adjusted under 35 U.S.C. 154(b) by 5 days.

(21) Appl. No.: 14/687,773

(22) Filed: Apr. 15, 2015

(65) Prior Publication Data

US 2016/0303379 A1    Oct. 20, 2016

(51) Int. Cl.
*A61N 1/00* (2006.01)
*A61N 1/05* (2006.01)
*A61N 1/36* (2006.01)
*A61N 1/368* (2006.01)
*A61N 1/08* (2006.01)

(52) U.S. Cl.
CPC ......... *A61N 1/0534* (2013.01); *A61N 1/3606* (2013.01); *A61N 1/36142* (2013.01); *A61N 1/36146* (2013.01); *A61N 1/0529* (2013.01); *A61N 1/0531* (2013.01); *A61N 1/36* (2013.01); *A61N 1/36082* (2013.01); *A61N 1/3686* (2013.01); *A61N 1/36103* (2013.01); *A61N 2001/083* (2013.01)

(58) Field of Classification Search
CPC ...... A61N 1/0529; A61N 1/0531; A61N 1/36; A61N 1/36103; A61N 1/3686; A61N 1/36146; A61N 1/36142; A61N 1/3606; A61N 1/0534; A61N 1/36082; A61N 2001/083
See application file for complete search history.

(56) References Cited

U.S. PATENT DOCUMENTS

| 2006/0264777 | A1* | 11/2006 | Drew | A61B 5/048 600/547 |
| 2009/0012593 | A1* | 1/2009 | Benabid | A61N 1/0531 607/116 |
| 2012/0290040 | A1* | 11/2012 | Moffitt | A61N 1/36142 607/45 |

* cited by examiner

*Primary Examiner* — Lindsey G Wehrheim

(57) ABSTRACT

The present disclosure provides neurostimulation systems and methods. A neurostimulation system includes at least one anode, at least one cathode, the at least one anode and the at least one cathode configured to apply electrical stimulation to a patient, and a controller electrically coupled to the at least one anode and the at least one cathode, the controller configured to determine when one of the at least one anode and the at least one cathode fails, measure, in response to the determination, a quantity indicative of a charge density of the applied electrical stimulation, compare the measured quantity to a predetermined limit, and perform at least one action when the measured quantity exceeds the predetermined limit.

4 Claims, 5 Drawing Sheets

SYSTEMS AND METHODS FOR MONITORING CHARGE DENSITY OF ELECTRICAL STIMULATION

FIELD OF THE DISCLOSURE

The present disclosure relates generally to stimulation methods and systems, and more particularly to monitoring charge density and electrode potential of applied stimulation.

BACKGROUND ART

Neurostimulation is a treatment method utilized for managing the disabilities associated with pain, movement disorders such as Parkinson's Disease (PD), dystonia, and essential tremor, and also a number of psychological disorders such as depression, mood, anxiety, addiction, and obsessive compulsive disorders. For example, deep brain stimulation (DBS) systems treat symptoms associated with movement disorders and psychiatric disorders by delivering electrical stimulation to a patient's brain.

Modern DBS systems are designed to deliver low-intensity electrical pulses to nerves/tissue in various combinations of amplitude, pulse width, and frequency. The electrical pulses travel from an implantable pulse generator (IPG), through leads and extensions, to electrodes near selected brain targets in order to provide therapeutic stimulation to one or both sides of the brain. To provide this stimulation, DBS systems are typically configured with a combination of an anode and one or more cathodes. As failure of one or more anodes or cathodes may result in an increased charge density, it would be desirable to accurately detect lead failure in a neurostimulation system.

BRIEF SUMMARY OF THE DISCLOSURE

In one embodiment, the present disclosure is directed to a neurostimulation system. The neurostimulation system includes at least one anode, at least one cathode, the at least one anode and the at least one cathode configured to apply electrical stimulation to a patient, and a controller electrically coupled to the at least one anode and the at least one cathode, the controller configured to determine when one of the at least one anode and the at least one cathode fails, measure, in response to the determination, a quantity indicative of a charge density of the applied electrical stimulation, compare the measured quantity to a predetermined limit, and perform at least one action when the measured quantity exceeds the predetermined limit.

In another embodiment, the present disclosure is directed to a method for operating a neurostimulation system. The method includes applying electrical stimulation to a patient using at least one anode and at least one cathode, determining, using a controller electrically coupled to the at least one anode and the at least one cathode, when one of the at least one anode and the at least one cathode fails, measuring, in response to the determination, a quantity indicative of a charge density of the applied electrical stimulation, comparing the measured quantity to a predetermined limit, and performing at least one action when the measured quantity exceeds the predetermined limit.

In another embodiment, the present disclosure is directed to a deep brain stimulation (DBS) system. The DBS system includes at least one anode, at least one cathode, the at least one anode and the at least one cathode configured to apply electrical stimulation to a brain of a patient, and an implantable pulse generator (IPG) electrically coupled to the at least one anode and the at least one cathode. The implantable pulse generator is configured to measure an impedance between the at least one anode and the at least one cathode, determine when the measured impedance falls outside a predetermined range, measure, in response to the determination, a charge density of the applied electrical stimulation, compare the measured charge density to a predetermined limit, and perform at least one action when the measured charge density exceeds the predetermined limit.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The systems and methods described herein facilitate monitoring charge density of applied stimulation. A neurostimulation system includes at least one anode, at least one cathode, and a controller electrically coupled to the at least one anode and the at least one cathode. The controller is configured to determine when one of the at least one anode and the at least one cathode fails, and address, in response to the determination, changes in charge density due to the failure.

Neurostimulation systems are devices that generate electrical pulses and deliver the pulses to nerve tissue of a patient to treat a variety of disorders. Neurostimulation systems include deep brain stimulation (DBS) systems and spinal cord stimulation (SCS) systems.

Figure 1:
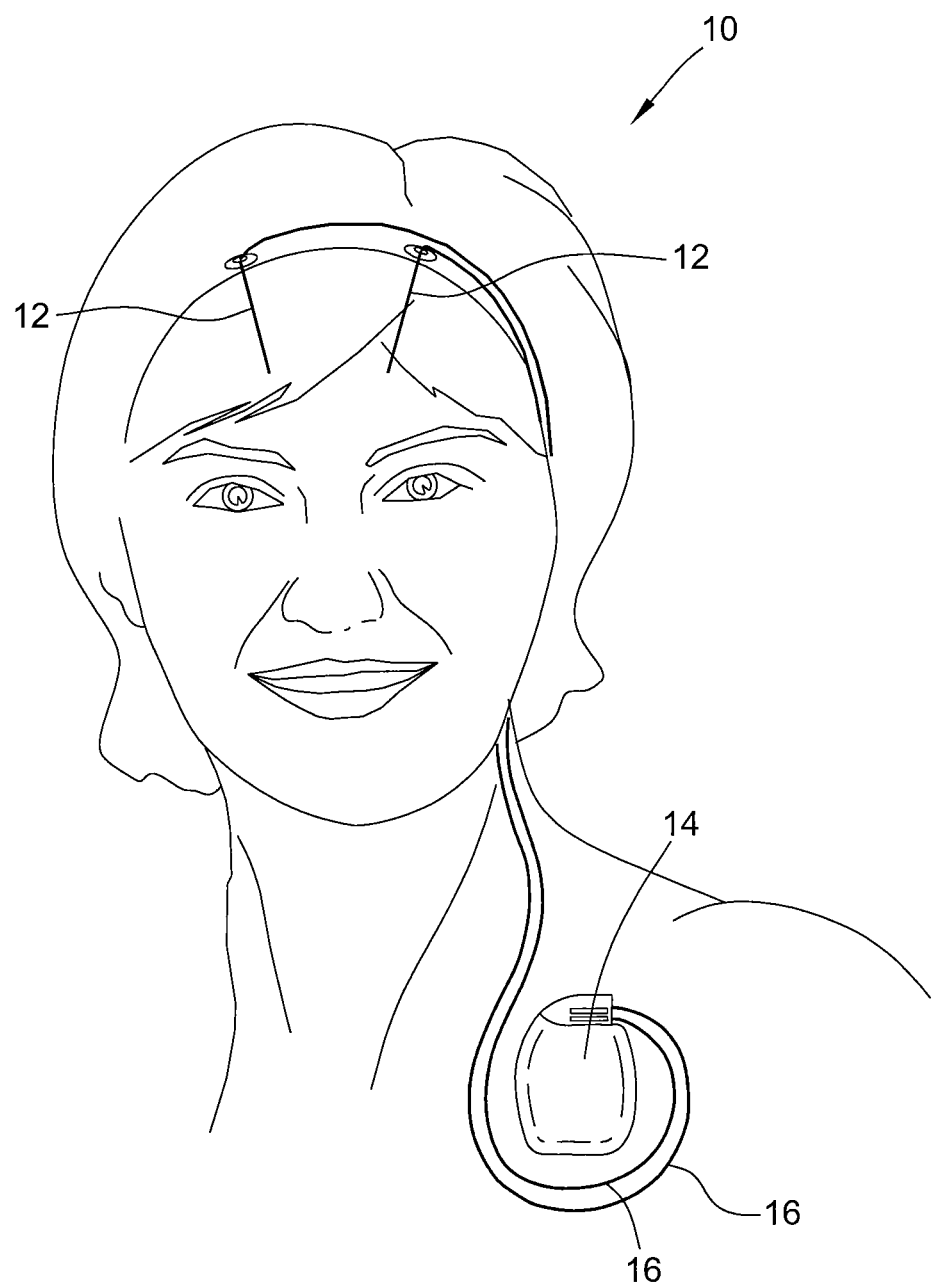
FIG. 1 is a schematic view of one embodiment of a deep brain stimulation system.

Referring now to FIG. 1, a DBS system is indicated generally at 10. System 10 includes a plurality of DBS leads 12 electrically coupled to a stimulation device 14 using associated extensions 16. Stimulation device 14 controls the delivery of electrical pulses to the brain of the patient, or subject, via DBS leads 12. In some embodiments, DBS system 10 includes one or more directional leads. For some diseases treated with DBS, patients rely on neurostimulation to provide symptom control. For example, for patients with Parkinson's disease, loss of DBS may lead to akinetic crisis. In contrast, for patients that use DBS for tremor control, stimulation loss may merely be inconvenient.

In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Peripheral nerve field stimulation (PNFS) is another form of neuromodulation. The basic devices employed for PNFS are similar to the devices employed for SCS including pulse generators and stimulation leads. In PNFS, the stimulation leads are placed in subcutaneous tissue (hypodermis) in the area in which the patient experiences pain. Electrical stimulation is applied to nerve fibers in the painful area. PNFS has been suggested as a therapy for a variety of conditions such as migraine, occipital neuralgia, trigeminal neuralgia, lower back pain, chronic abdominal pain, chronic pain in the extremities, and other conditions.

Figure 2:
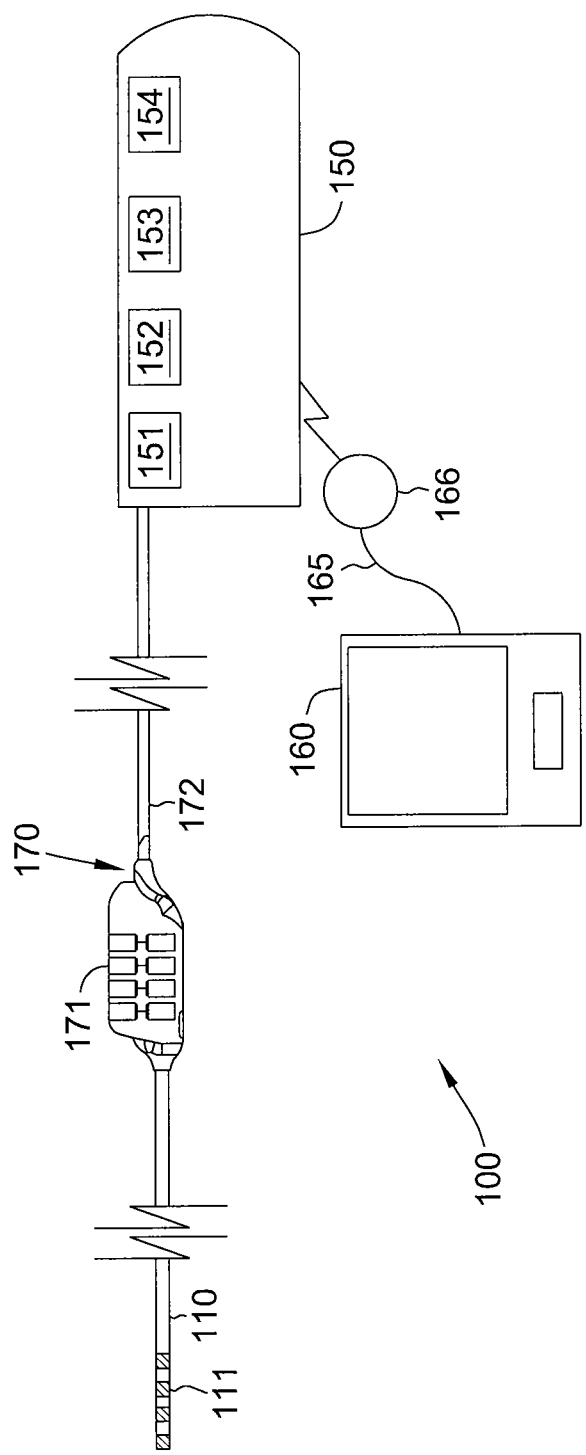
FIG. 2 is a schematic view of one embodiment of a stimulation system.

Referring now to FIG. 2, a stimulation system is indicated generally at 100. Simulation system 100 may be, for example, a DBS system or an SCS system. Stimulation system 100 generates electrical pulses for application to tissue of a patient, or subject, according to one embodiment. System 100 includes an implantable pulse generator 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of pulse generator 150 for execution by the microcontroller or processor to control the various components of the device.

Pulse generator 150 may comprise one or more attached extension components 170 or be connected to one or more separate extension components 170. Alternatively, one or more stimulation leads 110 may be connected directly to pulse generator 150. Within pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from pulse generator 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

Figure 3A:
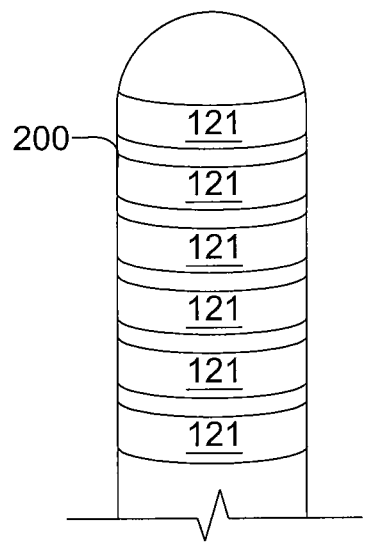
FIGS. 3A-3C are schematic views of stimulation portions that may be used with stimulation system of FIG. 2.
Figure 3B:
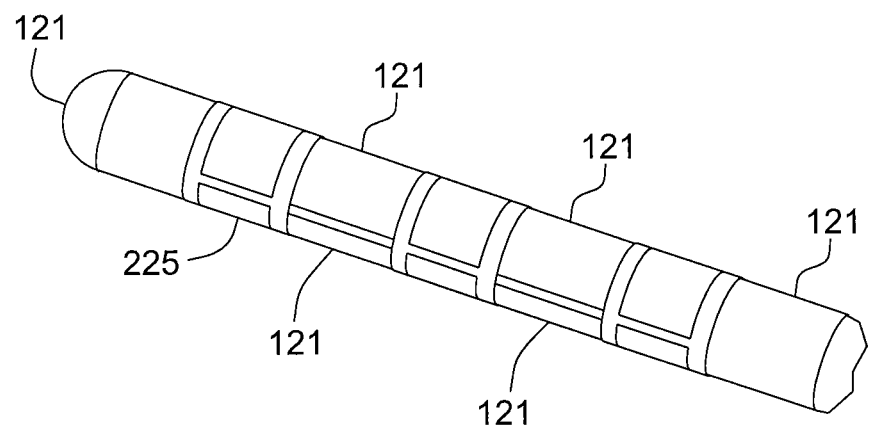
Figure 3C:
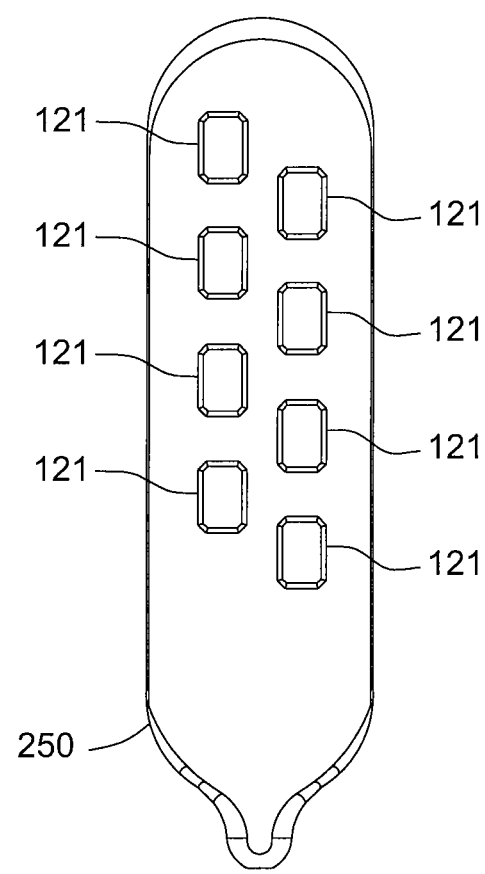

FIGS. 3A-3C respectively depict stimulation portions 200, 225, and 250 for inclusion at the distal end of lead 110. Stimulation portions 200, 225, and 250 each include a plurality of electrodes 121. Stimulation portion 200 depicts a conventional stimulation portion of a "percutaneous" lead with multiple ring electrodes 121. Stimulation portion 225 depicts a stimulation portion including several "segmented electrodes" 121. The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2011/0072657, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes 121 on a paddle structure.

Controller device 160 may be implemented to recharge battery 153 of pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of generator 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of pulse generator 150 to be controlled by user after pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Example commercially available neurostimulation systems include the EON MINI™ pulse generator and RAPID PROGRAMMER™ device from St. Jude Medical, Inc. (Plano, Tex.). Example commercially available stimulation leads include the QUATTRODE™, OCTRODE™, AXXESS™, LAMITRODE™, TRIPOLE™, EXCLAIM™, and PENTA™ stimulation leads from St. Jude Medical, Inc.

In stimulation portions 200, 225, and 250, for example, failure of one or more electrodes 121 may result in an increased charge density for the applied electrical stimulation. Specifically, charge density may be expressed as the product of a pulse width of the applied stimulation and an amplitude of the applied stimulation, divided by an active electrode surface area (i.e., the surface area of electrodes used in applying the stimulation). Accordingly, if one or more electrodes 121 fail, the stimulation parameters (i.e., pulse width and amplitude) remain constant, but the active electrode surface area decreases, which increases the charge density. Unexpected increases in charge density may be detrimental to the patient.

The embodiments described herein facilitate detecting failure of one or more electrodes and corresponding changes in charge density, and taking appropriate action in response to those detections. The methods described herein may be implemented, for example, using controller 151 (shown in FIG. 1).

Figure 4:
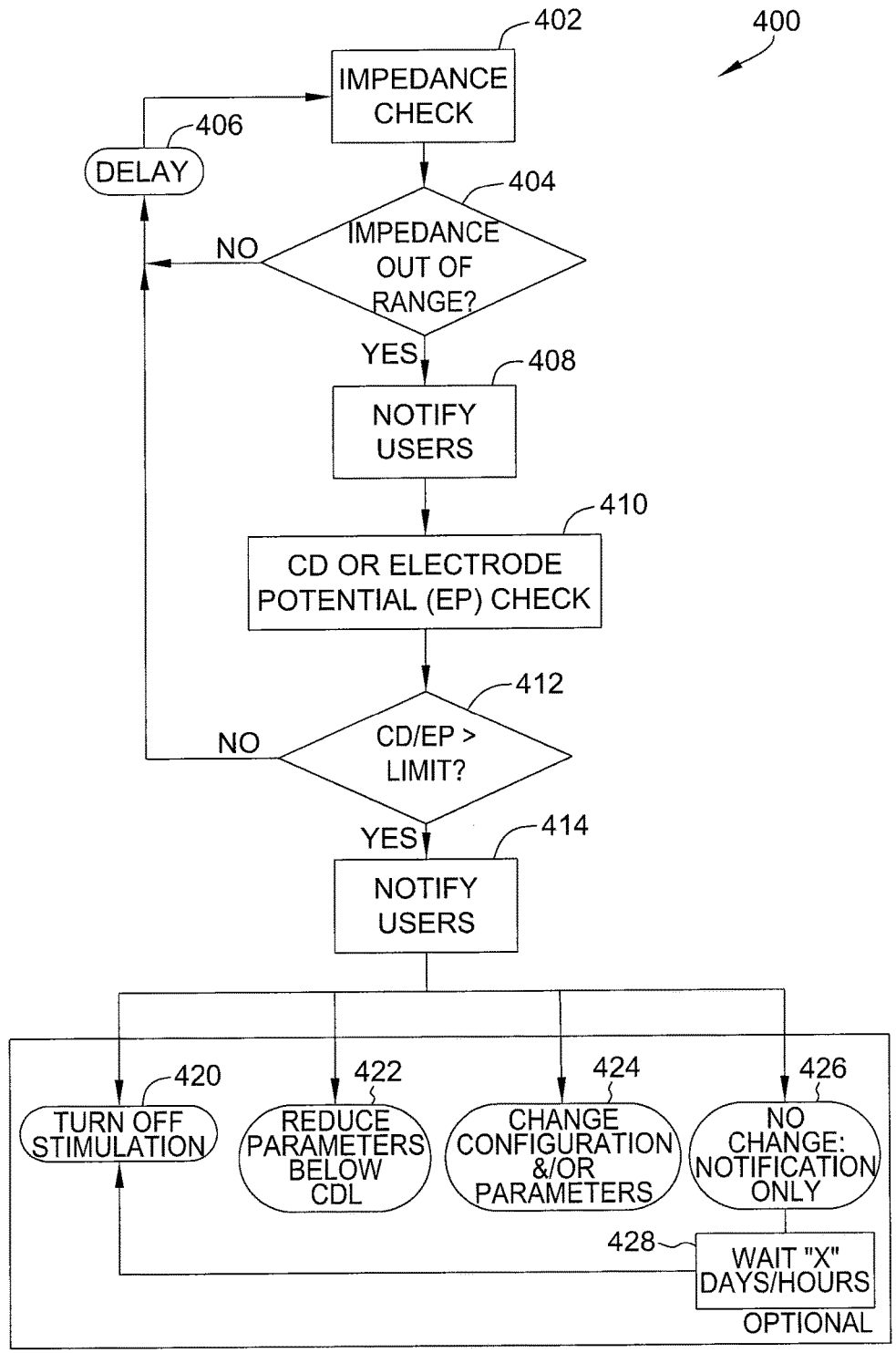
FIG. 4 is a flow diagram of one embodiment of a method for monitoring lead failure and charge density.

FIG. 4 is a flow diagram of a method 400 for monitoring lead failure and charge density in a neurostimulation system. Although method 400 is described in the context of a neurostimulation system, those of skill in the art will appreciate that method 400 may be applied to any system including reconfigurable electrodes functioning as more than one anode and cathode. Method 400 begins by measuring (i.e., checking) 402 an impedance between electrodes in the neurostimulation system. The impedance may be measured, for example, by generating a relatively small, subthreshold pulse, measuring the voltage and current of that pulse, and calculating the impedance from the measured voltage and current. The measured impedance is then compared 404 to a predetermined impedance range. The predetermined impedance range may be stored, for example, in memory of IPG 150. In some embodiments, the predetermined impedance range may be, for example a range from approximately 200 Ohms to 3000 Ohms. Of course, the predetermined impedance range may vary based on the particular application and/or type of lead used.

If the measured impedance falls within the predetermined impedance range, after a delay 406 (e.g., 30 seconds), the impedance is measured 402 again. If the measured impedance does not fall within the predetermined impedance range, this indicates that at least one electrode in the neurostimulation system has likely failed. Accordingly, a user (e.g., the physician and/or patient) is notified 408. The notification may include, for example, any suitable visual and/or audio cues. Further, the notification may be generated, for example, by controller device 160.

In this embodiment, an impedance between electrodes is measured 402 and compared 404 to a predetermined range. Alternatively, other electrical characteristics of the neurostimulation system may be analyzed. For example, in some embodiments, a voltage between electrodes is measured and compared to a predetermined voltage range. Further, in other embodiments, a current flowing between electrodes is measured and compared to a predetermined current range.

After notifying 408 users that the measured electrical characteristic falls outside the predetermined range, a charge density or electrode potential for the neurostimulation system is measured 410 (i.e., checked). The measured charge density and electrode potential are both quantities representative of the charge density of the neurostimulation system. To measure 410 charge density, charge density may be calculated, for example, based on known pulse amplitudes, pulse widths, and electrode surface area. To measure 410 electrode potential, controller 151 may look at, for example, voltage drops in the neurostimulation system immediately after electrical stimulation is applied. The measured charge density and/or electrode potential is then compared 412 to a predetermined limit. The predetermined limit may be stored, for example, in memory of IPG 150. For a DBS system, the predetermined limit for the measured charge density may be, for example, approximately 30 micro-Coulombs per square centimeter ($\mu C/cm^2$). For a SCS system, the predetermined limit for the measured charge density may be, for example, approximately 100 $\mu C/cm^2$.

If the measured charge density and/or electrode potential does not exceed the predetermined limit, after delay 406, the impedance is measured 402 again. If the measured charge density and/or electrode potential does exceed the predetermined limit, the charge density may be sufficient to damage tissue. Accordingly, a user (e.g., the physician and/or patient) is notified 414. The notification may include, for example, any suitable visual and/or audio cues. Further, the notification may be generated, for example, by controller device 160.

After the notification is generated, IPG 150 performs one or more actions. The number and type of actions performed may be preprogrammed such that they occur automatically, selected in advance by a user such that they occur automatically, selected by a user in response to being notified 414, and/or specified based on any other suitable criteria. For example, one potential action is stopping 420 application of electrical stimulation. Another action is reducing 422 at least one stimulation parameter to decrease the charge density. For example, the pulse width and/or amplitude of the applied electrical stimulation may be reduced by a predetermined amount, or may be reduced until the measured charge density and/or electrode potential falls below the predetermined limit.

Yet another potential action is changing 424 an electrode configuration of the neurostimulation system. For example, the combination of anodes and cathodes currently being used to apply stimulation may be switched to a different combination (e.g., by changing to a different active electrode). Moreover, another potential action is making 426 no changes to the stimulation parameters or electrode configuration, but merely notifying 414 a user. When no changes are made 426, after waiting 428 a predetermined period of time, application of electrical stimulation is stopped 420 if the measured charge density and/or electrode potential continues to exceed the predetermined limit. For any of the above-listed actions, a user may be notified (e.g., via controller device 160) when the respective action is performed. Further, the actions performed may be customized by the physician to fit the needs of each individual patient.

Notably, method 400 applies to neurostimulation systems that include more than one anode and cathode. For systems including a single anode and a single cathode (i.e., two total electrodes), if one of the two electrodes fails, stimulation ceases immediately.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A deep brain stimulation (DBS) system for applying electrical simulation to a patient, the DBS system comprising:

at least one stimulation lead comprising a plurality of segmented electrodes; and an implantable pulse generator (IPG) for generating electrical pulses, the IPG adapted to apply the electrical pulses to tissue, of the patient using, electrodes of the at least one stimulation lead, wherein the IPG is configured to:

simultaneously apply the electrical pulses to tissue of the patient using multiple segmented electrodes of the plurality of segmented electrodes, the multiple segmented electrodes operating at a first polarity according to a stimulation program, wherein the electrical pulses are applied using the multiple segmented electrodes using a common current source of the IPG;

measure an impedance of current flow through the multiple segmented electrodes for the common current source during operation according to the stimulation program;

determine a segmented electrode failure within the multiple segmented electrodes based on the measured impedance;

measure, in response to the determination, a charge density of the applied electrical pulses for a number of segmented electrodes that is less than a number of electrodes in the multiple segmented electrodes used for stimulation before occurrence of the segmented electrode failure;

compare the measured charge density to a predetermined limit; and perform at least one action when the measured charge density exceeds the predetermined limit.

2. The DBS system of claim 1, wherein the predetermined limit is approximately 30 micro-Coulombs per square centimeter.

3. The DBS system of claim 1, wherein to perform the at least one action, the IPG is configured to stop applying electrical stimulation.

4. The DBS system of claim 1, wherein to perform the at least one action, the IPG is configured to reduce at least one of a pulse width and an amplitude of the applied electrical pulses.

* * * * *